(12) United States Patent
Anderson et al.

(10) Patent No.: US 9,610,140 B2
(45) Date of Patent: *Apr. 4, 2017

(54) ORTHODONTIC ALIGNER FABRICATION BY OVERLAY METHOD

(71) Applicant: DENTSPLY SIRONA INC., York, PA (US)

(72) Inventors: Michael C. Anderson, Palmetto, FL (US); Bradford H. Clatt, Bredenton, FL (US); Jack Keith Hilliard, Lakeland, FL (US); Daniel Julié, Marseilles (FR)

(73) Assignee: Dentsply Sirona Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,423

(22) Filed: Apr. 19, 2016

(65) Prior Publication Data

US 2016/0228216 A1    Aug. 11, 2016

Related U.S. Application Data

(63) Continuation of application No. 13/391,322, filed as application No. PCT/US2010/046175 on Aug. 20, 2010, now Pat. No. 9,345,557.

(Continued)

(51) Int. Cl.
*A61C 3/00* (2006.01)
*A61C 7/08* (2006.01)
(Continued)

(52) U.S. Cl.
CPC ............... *A61C 7/08* (2013.01); *A61C 7/002* (2013.01); *A61C 9/00* (2013.01)

(58) Field of Classification Search
CPC .. A61C 7/08; A61C 7/002; A61C 9/00; A61C 7/006; A61C 7/06; A61C 7/008
See application file for complete search history.

(56) References Cited

U.S. PATENT DOCUMENTS

| 2,479,780 | A  | 8/1949 | Remensnyder |
| 6,293,790 | B1 | 9/2001 | Hilliard |

(Continued)

FOREIGN PATENT DOCUMENTS

| JP | 2008/307281 A  | 12/2008 |
| WO | 2005/092234 A1 | 10/2005 |

(Continued)

*Primary Examiner* — Heidi M Eide
(74) *Attorney, Agent, or Firm* — McNees Wallace & Nurick LLC

(57) ABSTRACT

The orthodontic alignment of misaligned teeth includes preparing a digital and/or physical overlay model which is the superimposed positioning of the patient's original misaligned dentition with the target or final position. The superimposition of one upon the other creates an open space through which teeth may move in a natural manner, allowing for a treatment plan that takes into account the physical interaction of one tooth with another or the differences in tooth movement rates due in part to differences in underlying bone density or the like. An aligner tray fabricated using the model will likewise represent the before and after tooth positions and will also have the open space to allow tooth movement. Force exerting structures are preferably placed into the aligner tray to impinge upon the patient's teeth in a prescribed manner when the aligner tray is inserted into the patient's oral cavity.

10 Claims, 12 Drawing Sheets

Related U.S. Application Data

(60) Provisional application No. 61/307,668, filed on Feb. 24, 2010, provisional application No. 61/274,821, filed on Aug. 21, 2009.

(51) Int. Cl.
*A61C 7/00* (2006.01)
*A61C 9/00* (2006.01)

(56) References Cited

U.S. PATENT DOCUMENTS

| | | |
|---|---|---|
| 6,702,575 B2 | 3/2004 | Hilliard |
| 7,077,646 B2 | 7/2006 | Hilliard |
| 2002/0010568 A1 | 1/2002 | Rubbert et al. |
| 2005/0048433 A1 | 3/2005 | Hilliard |
| 2006/0008760 A1 | 1/2006 | Phan et al. |
| 2006/0177789 A1 | 8/2006 | O'Bryan |
| 2006/0188834 A1 | 8/2006 | Hilliard |
| 2007/0065768 A1 | 3/2007 | Nadav |
| 2008/0102415 A1 | 5/2008 | Scott |
| 2011/0159451 A1 | 6/2011 | Kuo et al. |

FOREIGN PATENT DOCUMENTS

| | | |
|---|---|---|
| WO | 2008/026064 A2 | 3/2008 |
| WO | 2008/032310 A2 | 3/2008 |
| WO | 2009/103887 A1 | 8/2009 |

ORTHODONTIC ALIGNER FABRICATION BY OVERLAY METHOD

CROSS-REFERENCE TO RELATED APPLICATIONS

This application is a continuation of U.S. Ser. No. 13/391,322 which is a national stage application of PCT/US2010/046175 filed Aug. 20, 2010 and which claims the benefit of U.S. Provisional Application No. 61/274,821 filed Aug. 21, 2009, entitled "ORTHODONTIC ALIGNER AND METHOD"; and U.S. Provisional Patent Application No. 61/307,668 filed Feb. 24, 2010 entitled "ORTHODONTIC ALIGNER FABRICATION BY OVERLAY METHOD", all of which are hereby incorporated by reference in their entirety.

TECHNICAL FIELD

The present invention generally relates to the field of orthodontics. More particularly, the invention relates to an orthodontic alignment tray and a method for fabricating such a tray and aligning teeth using manual or digital programming techniques.

BACKGROUND OF THE INVENTION

The field of orthodontics is well developed. Using conventional brackets, wires and the like, and based upon the nature of a patient's misaligned teeth, a dental professional can determine a pathway for applying appropriate forces to move teeth into better alignment. As the teeth are moved in such conventional procedures, they will often be blocked by other teeth. Because of the initial misalignment, it is often not simply a matter of moving, or repositioning, a tooth in one direction to correct its position. Rather, the treatment plan most often must account for physical contact between teeth as they move.

There have been developed methods of correcting the position of misaligned teeth using dental trays fabricated in a manner that a given tray will itself exert a force upon the misaligned teeth to cause movement. These include for example, the Invisalign® trays from Align Technology, Inc. of Santa Clara, Calif. Often these alignment trays are fabricated from a clear plastic material, and are provided in a series such that each succeeding tray moves the teeth more or differently than the previous tray, in an incremental fashion so as to effect the prescribed treatment plan. Each tray therefore, will move certain teeth from a starting or "before" position to a selected ending or "after" position. The "after" position is based solely upon the nature of the immediately previous "before" position. Further, the shape and force exerted by each successive aligner tray in the treatment process of the conventional system is based only upon the nature of where the previous tray left off in the moving of the teeth. There may be some target goal in mind as to where the dental professional wants to ultimately move the teeth, but until the very end of the patient's treatment procedure, this final position and the initial starting position do not affect the incremental or intermediate treatment steps. That is, the conventional system can be said to be "closed."

Because of this, it has often been necessary therefore, to apply excessive stripping to teeth in order to allow them to move in the approximate direction desired. The results of excessive stripping are often not aesthetically appealing or even healthy for the stripped teeth. While the conventional procedures will move teeth, they do not permit the teeth to move in their more natural or open pathways.

It would be advantageous therefore, for an alignment tray to be fabricated and used in a manner that allows for the open or natural movement of teeth. That is, the tray and the resulting procedure should more readily and appropriately accommodate the variables to tooth movement including not only the initial misaligned position of a given tooth and the final desired position, but also the physical interaction that exists between teeth or that will occur as the teeth move, the variable nature of the underlying bone structure and the like. Heretofore, conventional orthodontic aligner trays have not allowed for this type of natural tooth movement in orthodontic procedures.

Another practice used by orthodontists involves altering a polymeric shell-type aligner beyond its original as-formed configuration. Typically the interior, tooth-contacting surfaces of tooth-accommodating compartments are formed in an aligner. The inside surface of any one compartment completely surrounds and is in intimate contact with its tooth when the appliance is seated in position. For forces such as those created through the installation of a single bump in an interior wall of an aligner to be effective in moving the tooth, the interior wall on the opposite side of the compartment must be relieved or removed to allow the tooth to move in that direction. The tooth will not move unless obstacles have been cleared and free space is provided for that tooth to move into. To handle such situations, orthodontists may alter aligners by cutting away material or blocking out portions of a tooth model, to create free space for a tooth to move into. Free space or windows are created by trimming away aligner material in the direction of desired tooth movement. A window in an aligner will be created for example on the labial side of a tooth if the treatment plan requires that a bump be formed on the lingual side. It would be advantageous as well to provide an aligner tray with tooth compartments that include space into which the targeted teeth may move, without having to manually cut away tray material or block out portions of a tooth model when forming the tray.

DISCLOSURE OF THE INVENTION

It is therefore, an object of the present invention to provide an aligner tray fabricated and used in such a manner as to accommodate the natural or open movement of teeth. This and other objects of the invention as will become apparent from the description to follow, are carried out by the invention as hereinafter described and claimed.

According to the invention, an alignment tray is fabricated based upon a model that is a physical overlay of both the initial misalignment (or an intermediate one) and a target or final position of the teeth where they are ultimately desired to be moved. The model can be a physical model, a digital model or both. A tray fabricated from such an overlay model will have a force bump or appliance of some kind that is placed into the tray to exert a selected force upon selected teeth to cause them to move as desired. The tray therefore, is itself an overlay that includes both the starting point of the teeth and the end point, but it is the force exerting bumps or appliances fabricated into the inventive trays that exert the tooth moving force. Because of this arrangement, the tray is an open system and allows for the more natural movement of teeth that are resisted by the nature of the underlying bone structure and by interaction with other teeth. Physical contact between teeth, different movement rates based upon such bone density and the like, are not only permitted but will be proactively planned for and even employed by the dental professional's prescription to effect the overall treatment procedure.

In one embodiment, a method of fabricating orthodontic aligner trays includes acquiring an original digital model of a patient's teeth; segmenting the teeth represented by the digital model; repositioning at least one of the teeth into correct alignment to create a final teeth model, the final teeth model representing a final teeth position; superimposing the final teeth model with the original digital model to create a digital overlay model, the overlay model comprising a starting point defined by the original digital model and an end point defined by the final teeth model; fabricating at least one aligner tray based on the overlay model to define a tooth-receiving compartment within each aligner; and inserting at least one force appliance into the at least one aligner tray, the at least one force appliance positioned within the tooth-receiving compartment to exert a selected force upon selected teeth.

In another embodiment there is an aligner tray for repositioning teeth according to an orthodontic treatment plan. The aligner tray includes a tray portion defining a tooth-receiving compartment within the tray portion and formed from a thermoformable plastic sheet. The tooth-receiving compartment is based on an overlay model. The overlay model includes an original teeth position, a final teeth position and path ways for each tooth. The original teeth position, the final teeth position and path ways for each tooth fall within the tooth-receiving compartment of the aligner tray. The final teeth model represents at least one segmented teeth being repositioned into correct alignment to create a final teeth model. The final teeth model is superimposed with the original digital model. Force appliances are positioned within the tooth-receiving compartment to exert a selected force upon selected teeth.

In yet another embodiment, a method of fabricating orthodontic aligner trays includes pouring a stone model of a patient teeth and scanning the stone model into a digital file using a scanning software system; segmenting the teeth represented by the digital model; measuring the tooth and arch width digitally; analyzing a case using inter-proximal reduction prescription (IPR) and desired tooth movements, reviewing IPR prescription for validity; performing IPR if prescription is acceptable; and developing and communicating a treatment plan; repositioning at least one of the teeth into correct alignment to create a final teeth model, the final teeth model representing a final teeth position; superimposing the final teeth model with the original digital model to create a digital overlay model, the overlay model comprising a starting point defined by the original digital model and an end point defined by the final teeth model; creating a rapid prototype model for a plurality of identical aligner trays based on the overlay model to define a tooth-receiving compartment within each aligner; vacuum thermoforming each of the aligner trays over the physical overlay model using a vacuum forming machine and a plastic thermoforming sheet; programming at least one force appliance in at least one aligner tray to incrementally reposition the selected teeth incrementally according to the treatment plan; and inserting the at least one force appliance into the at least one aligner of the plurality of aligner trays, the at least one force appliance positioned within the tooth-receiving compartment to exert a selected force upon selected teeth.

PREFERRED EMBODIMENT FOR CARRYING OUT THE INVENTION

A method according to the present invention includes several steps. Not all of the following steps are necessary and there are alternatives. For example, although the invention will be characterized as employing, for example, a digital dental model and software to create the inventive models and aligners, it will be appreciated that the procedures can be accomplished manually. Similarly, fabrication methods of physically creating the various inventive components can be by conventional rapid prototyping procedures or the like as will be discussed, again with the understanding that other fabrication techniques can be employed within the scope of the invention.

The inventive method employing the inventive components therefore, preferably includes receiving, obtaining or otherwise preparing a stone or plaster model of the patient's dentition or even a conventional dental impression thereof. While it is possible that the invention can be carried out by a dental professional, the invention will be described herein as being carried out in conjunction between a dental professional and an extension of the professional such as a laboratory. It is to be understood that no distinction should be made or implied as to such a division and the nature of the present invention is the whole, not the individual participants. Both a division between a dental professional and a laboratory and the carrying out of the invention by a single person or entity, or indeed between any multiple entities is within the scope of the invention without limitation.

When received, each case is inspected to ensure that all the proper materials are included with the shipment, including as may be employed, physical models, impressions, digital scans of the dentition or the like. Again, this may vary depending upon the above described division of labor and is not itself a necessary limitation of the invention. For example, cases that are received by a laboratory as impressions only will have stone models poured and then each model will be individually inspected to determine that the model is complete and an accurate representation of the patients dentition. Alternatively, if the model itself is received from an upstream source, then it will be so inspected. Digital scans of the dentition will be treated in the same manner.

Figure 1:
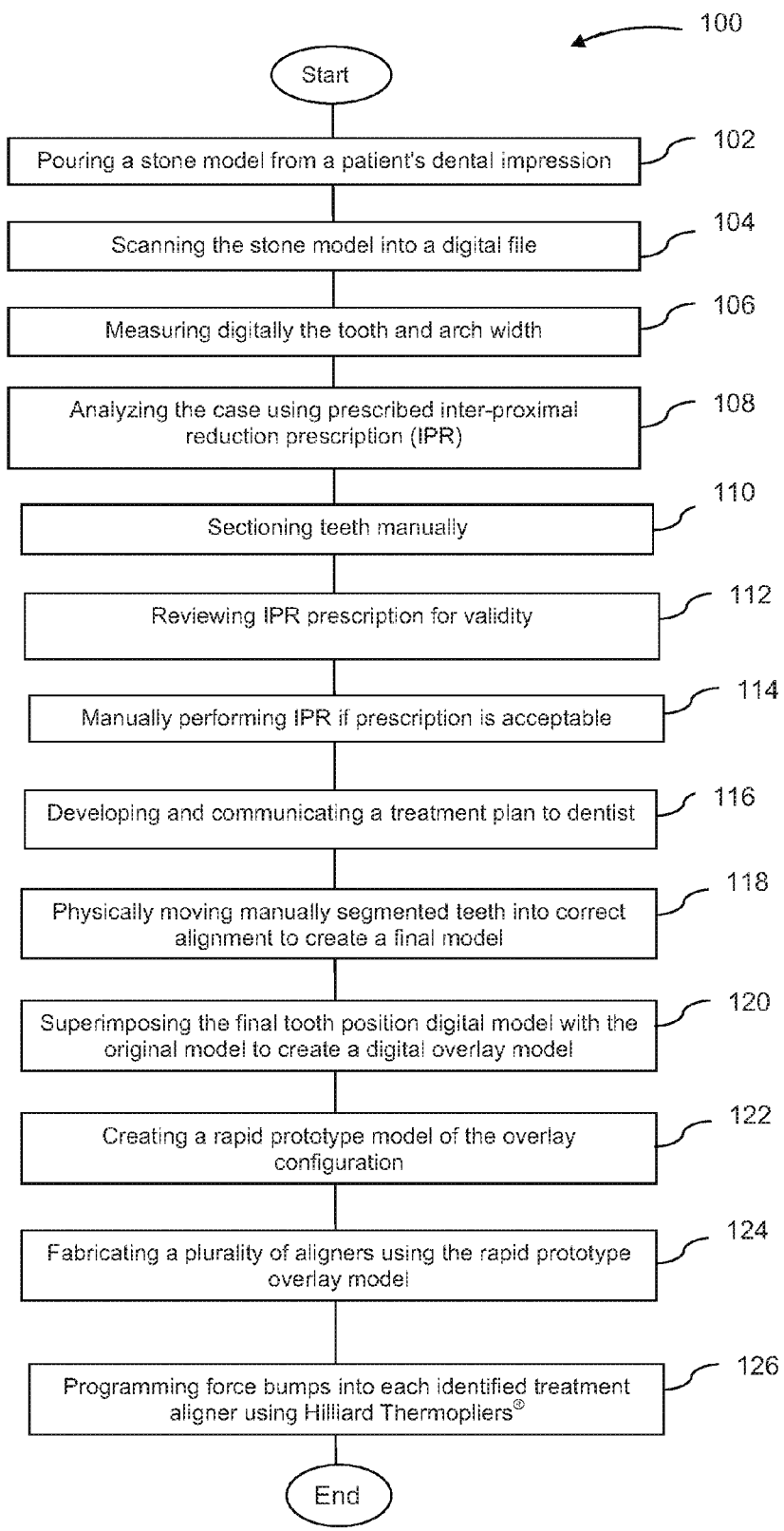
FIG. 1 shows a flow chart of one embodiment of the overlay method of fabricating aligner trays.
Figure 2:
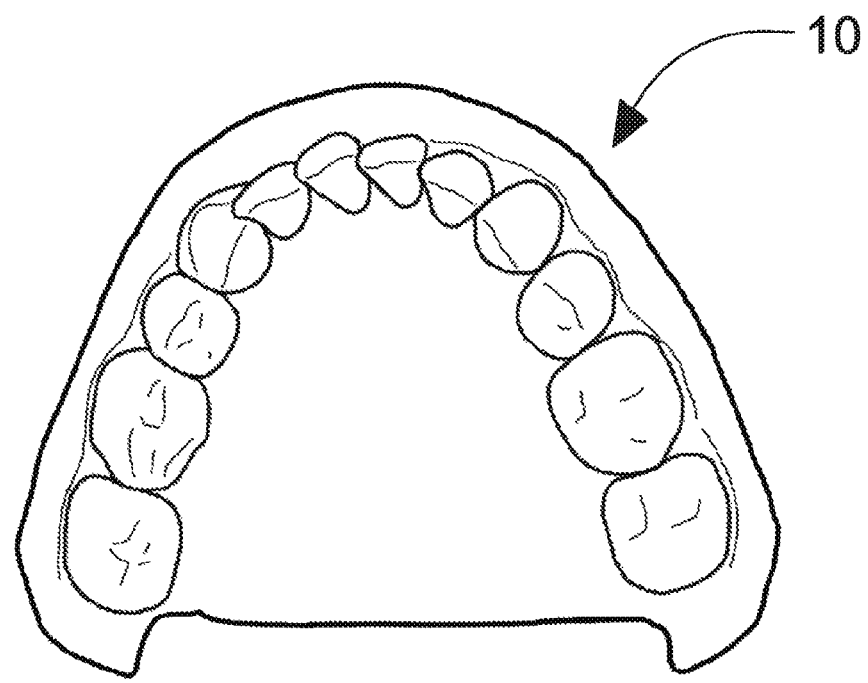
FIG. 2 is a top plan view of a model of a patient's dentition before orthodontic treatment according to the present invention.

Referring to FIG. 1, the overlay method, generally indicated as 100, for fabricating aligner trays for orthodontic treatment is described as follows. As described above, patient's dental impression is received and inspected. At step 102, a stone model 10 (FIG. 2) is poured from the impression. At step 104, stone model 10 is then scanned into a digital file, e.g., using a scanning software system such as 3Shape R700, by 3shape A/S, of Copenhagen, Denmark (hereinafter referred to as 3shape), a 3D scanner system developed to scan dental stone models. At step 106, the tooth and arch width are measured digitally, e.g., using Ortho Analyzer software. At step 108, the patient's malocclusion is analyzed using prescribed inter-proximal reduction prescription (IPR) and desired tooth movements. At step 110, representations of the teeth are manually sectioned or segmented using software, e.g., Ortho Analyzer Next Generation software from 3 shape.

The type of scanner or scanning is not necessarily a limitation of the present invention. One useful and commercially marketed scanner is, for example, the OrthoPlex orthodontic digital modeling solution available from DENTSPLY International of York, Pa. The OrthoPlex scanner and its associated software, creates a three-dimensional (3D) digital model that can be accessed by a computer or the like, and is stored as an STL file. An STL file is a conventional format often used by stereolithography software to generate information needed to produce 3D models on stereolithography machines. While it is not necessary to use this file format, the format is useful in conjunction with the present invention because of the preferred use of a stereolithography step as will be described below.

Figure 3:
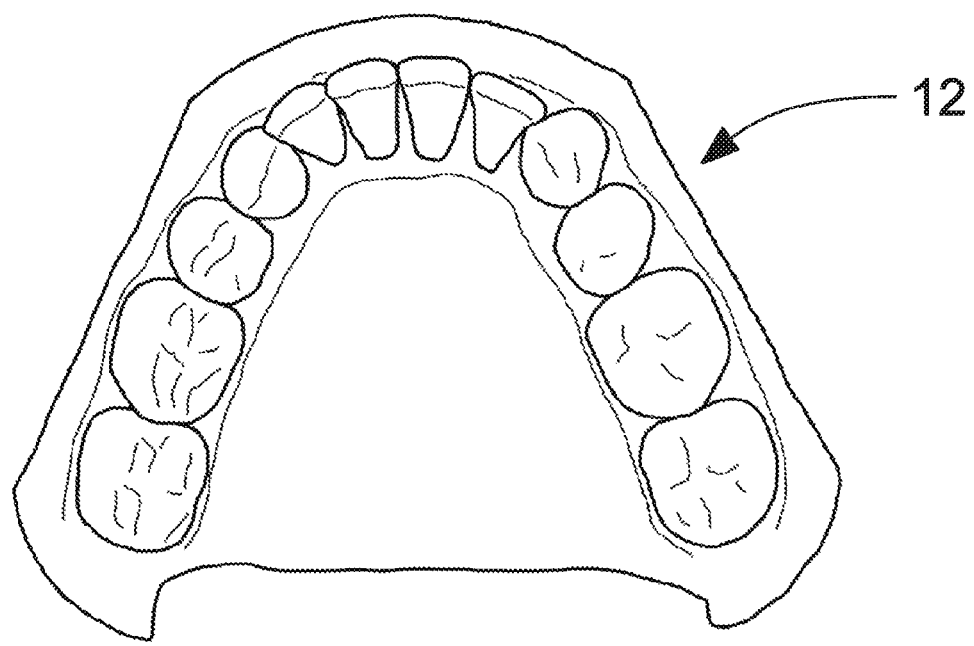
FIG. 3 is a top plan view of a model of a patient's dentition representative of the final tooth position which is the final or target position according to the prescribed orthodontic plan for the patient whose dentition is represented by the model of FIG. 2.
Figure 4:
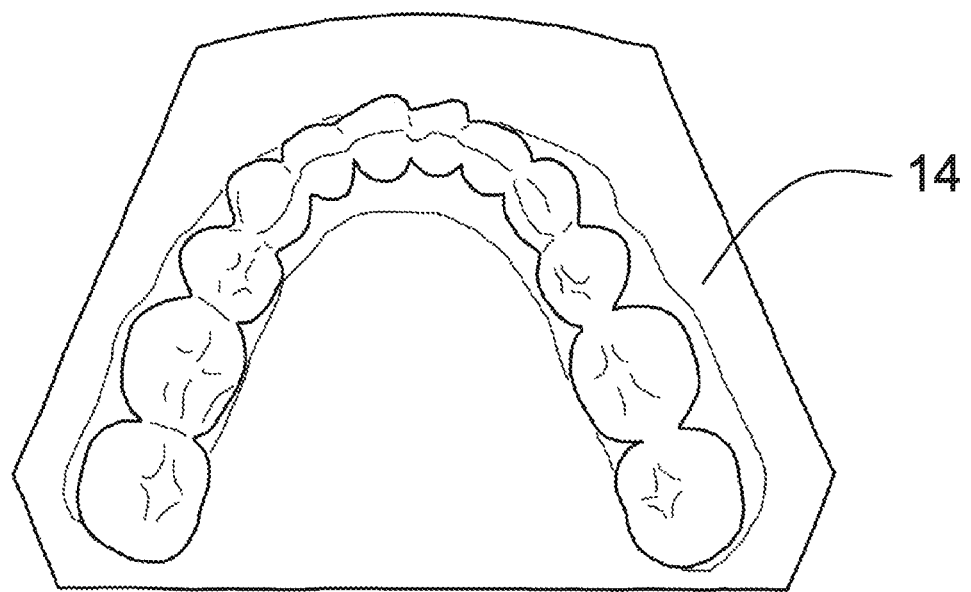
FIG. 4 is a top plan view of a digital representation of both the model of FIG. 2 and the model of FIG. 3 superimposed one upon the other, thereby creating space between the position of the teeth as in the model of FIG. 2 and the position of the teeth as in model of FIG. 3.
Figure 5A:
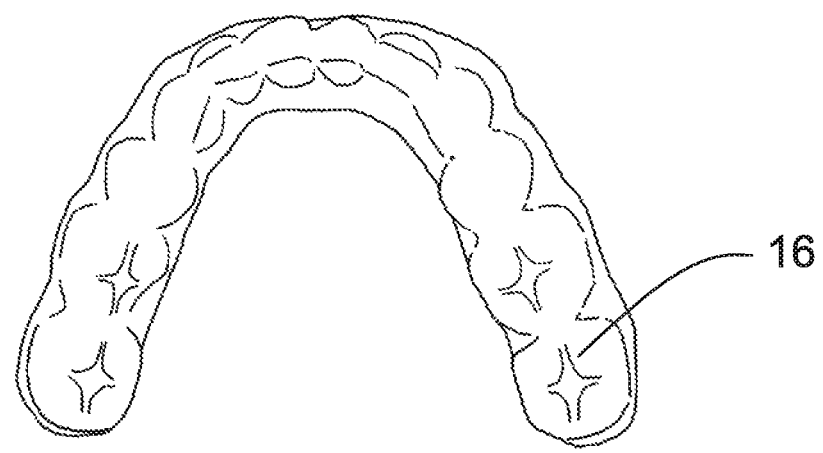
FIGS. 5a, 5b, 5c show multiple views of a physical overlay model of the digital superimposed model of FIG. 4.
Figure 5B:
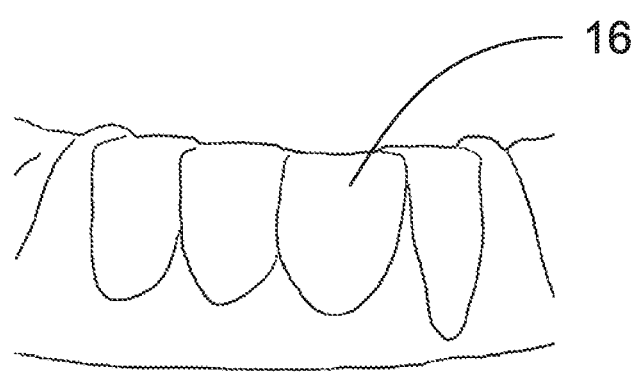
Figure 5C:
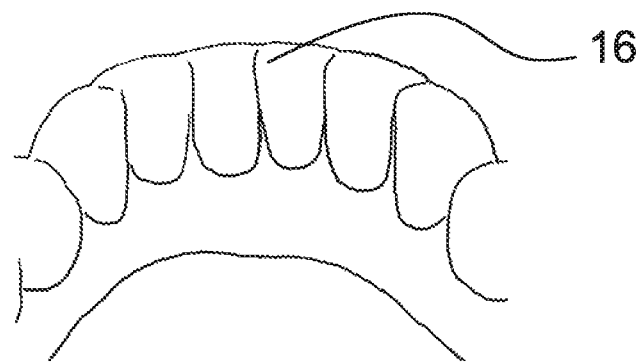

At step 112, the IPR prescription is reviewed for validity. Next, at step 114, if the prescription is acceptable the IPR is done manually, and necessary changes are approved by the dentist. At step 116, a treatment plan is developed and communicated to the dentist, using a set of clinical verification forms. Next, at step 118, the manually segmented representations of the teeth are physically moved into correct alignment to create a final model 12 (FIG. 3). Final model 12 may then be scanned to create a final tooth position digital model corresponding to final model 12. At step 120, the final tooth position digital model is superimposed with the digital model of the original model 10 to create a digital overlay model 14 (FIG. 4). In an exemplary embodiment digital overlay model 14 may be created using Materialise 3-matic, a custom software solution. The digital overlay model 14 may be suitable for rapid prototyping, e.g., using Materialise 3-matic. Next, at step 122, a rapid prototype or physical overlay model 16 (FIG. 5) is created of the overlay configuration.

Physical overlay model 16 is then created by a rapid prototyping method. The rapid prototyping technique should be understood to be all techniques whereby an object is built layer by layer or point per point by adding or hardening material (also called free-form manufacturing). The best known techniques of this type are: stereolithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; or fused deposition modeling, whereby a synthetic material is fused and is stacked according to a line pattern.

Figure 6:
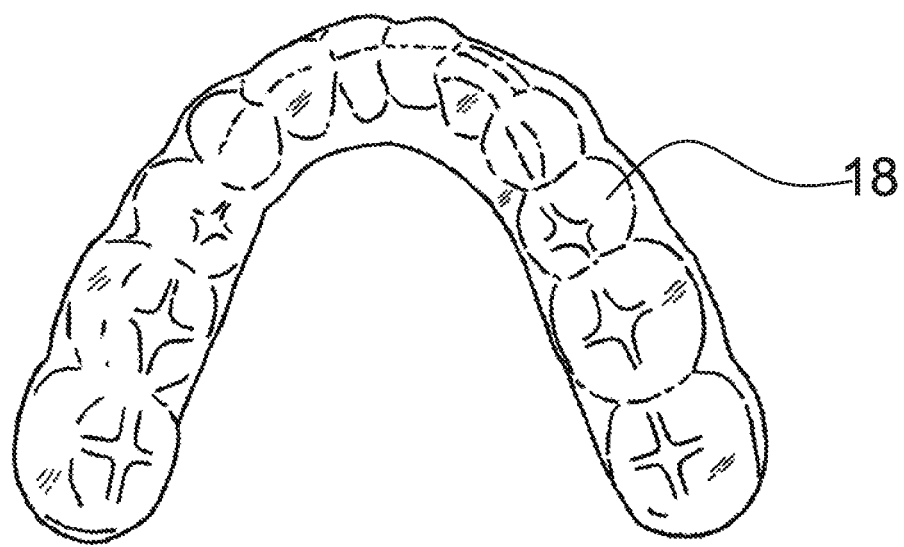
FIG. 6 is a top plan view of an aligner tray prepared from the physical overlay model of FIG. 5.

Next, at step 124, a plurality of identical aligner trays 18 (FIG. 6) are fabricated using the physical overlay model 16. The number of aligners varies from case to case. In one exemplary embodiment, aligner tray 18 is preferably thermo-formed over the physical overlay model 16 using, for example, an Essix vacuum forming machine and Essix Ace plastic thermoforming sheets. Both the sheets and the thermoforming machine are commercially available from DENTSPLY International, and the thermoforming process itself is conventional and known in the dental art. Using the physical overlay model 16 to produce aligner tray 18 results in a clear pathway of space from the teeth positions before patient treatment to the teeth positions after treatment, created to allow for tooth movement, as was already discussed.

Figure 7A:
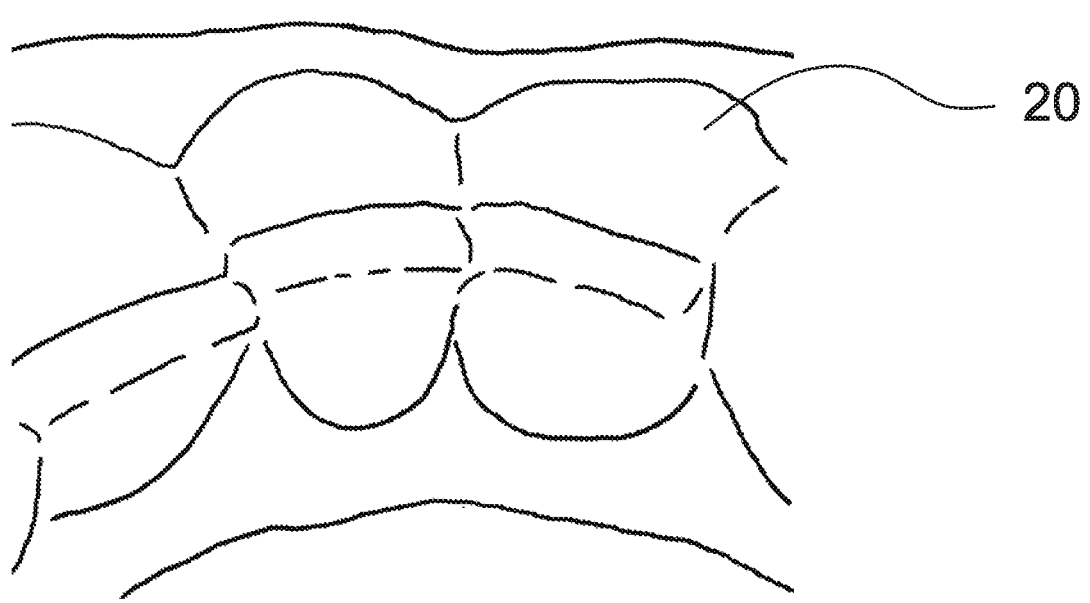
FIGS. 7a, 7b and 7c are close up views of one portion of the aligner of FIG. 6, with force bumps inserted therein.

At this point in the fabrication process, aligner tray 18 is passive, i.e., aligner tray 18 will not exert forces on the teeth when inserted into the patient's mouth. The original and the final tooth positions as well as the path ways for each tooth fall within the boundaries of the aligner. The aligner trays 18 are then thermoformed using the overlay model 16. Each aligner tray 18 is identified as step 1, 2, 3, etc. The resulting aligner tray 18 does not actively engage any single tooth for inducing tooth movement, but generates a passive aligner tray 18 with which preselected individual teeth can be moved. Movement of the preselected individual teeth is induced by programming or forming features in the passive aligner, such as bumps 20 (see, e.g., FIG. 7a), to apply pressure to teeth. Features may be formed, for example, by using the patented Hilliard thermoforming pliers system, which is disclosed in U.S. Pat. No. 6,293,790 issued Sep. 25, 2001 to Hilliard, and U.S. Pat. No. 7,077,646 issued Jul. 18, 2006 to Hilliard, both of which patents are incorporated herein by reference.

At step 126, after thermoforming aligner trays 18, force bumps 20 are programmed into each identified treatment aligner tray 18, e.g., as prescribed in a clinical verification plan from the treatment plan step. Programming force bumps 20 into aligner trays 18 may be done by manually thermoforming each bump 20 in the lab using a thermoforming tool, for example, a Hilliard Thermopliers®, available from DENTSPLY Raintree-Essix, of Sarasota, Fla. Aligner trays 18 that are thermoformed from overlay models 16 may be manually adjusted with the force bumps 20 using the Thermopliers®. Aligner trays 18, inclusive of the manual force bumps 20 are then sent to the dental professional. After the final aligner configuration is inspected, a final retainer is thermoformed using final model 12, and then aligner trays 18 and final retainer are shipped to the dentist.

It will be appreciated that the physical overlay model 16 may be created in a completely manual process by otherwise conventional techniques. In whatever manner the physical overlay model 16 is prepared, the result is that it is a representation of both the patient's starting teeth position and the target, final or end position, one superimposed upon the other. It will be appreciated that there is an open area or space between those structures representing the original tooth position and those structures representing the final tooth position. This open nature of the physical overlay model 16 allows for the above described natural movement of teeth and the taking into account the physical contact between teeth, differences in underlying bone density and the like, as will be appreciated from the following discussion concerning the preparation of an aligner tray 18 using physical overlay model 16. Of course, if desired, it would also be possible to control a fabrication machine using digital overlay model 14 directly to create an aligner tray 18, and still be within the scope of the invention.

After aligner tray 18 has been formed over physical model 16, aligner tray 18 may be removed and trimmed in a manner conventional with dental trays. Once the aligner tray 18 is trimmed, force exerting structures of some kind are placed into the aligner tray 18 in a manner to carry out the prescribed orthodontic tooth moving or repositioning procedure as the patient inserts the aligner tray 18 into the oral cavity and wears it therein for the prescribed length of time. For example, distortions in the tray material itself may be created to provide force bumps 20, preferably by the use of Hilliard thermo-forming pliers, also available from DENTSPLY International. The bumps are placed at predetermined locations to create the desired movement of each tooth according to the prescribed treatment plan. Each force bump 20 will push a tooth into the pathway of space in the aligner created by the use of the physical overlay model 16. It will be appreciated that force exerting structures may include additional plastic attachments, pins, buttons or indeed any structure useful and capable of applying an appropriate and selectable force in an orthodontically acceptable manner. The aligner tray 18 or a new aligner tray (not shown) can be provided to the patient having the force exerting structures adjusted according to the patient's treatment plan.

In another embodiment of the invention, an aligner tray 18 is prepared as above, but is provided with force exerting structure in the form of a flowable material that can be used to fill or partially fill the aligner tray 18. The flowable material can be shaped or even selectively hardened to provide the desired force to be exerted upon the selected tooth or teeth to carry out the prescribed treatment plan. It is even possible that flowable materials of different durometer ratings or viscosities can be provided to achieve parts or different parts of the overall patient treatment plan. In a similar fashion, in the instance where there is a void or space between teeth, or perhaps where extra space is needed, the physical overlay model 16 may be covered or partially covered in such a material, or even a standard dental impression material, such that additional or different selected space may be introduced into the subsequently fabricated aligner tray 18.

U.S. Pat. No. 6,293,790 entitled "Heated Orthodontic Pliers", and incorporated by reference, discloses a series of steel dental pliers useful for modifying polymeric shell aligners. Thermopliers® refers to a group of hand-held steel instruments that in use are heated to a predetermined temperature. Once heated, they are directed to an aligner to effect local heat-softening and thermal flowing of the aligner structure thereby forming various types of useful features and alterations.

Rotations, in contrast to torqueing and tipping-type corrective forces, are more difficult to deliver using aligners. To augment an aligner's capability to fully correct a rotation, orthodontists use one of the set of Thermopliers® configured to thermoform a small, sharp, inward-facing bump 20 in the structure of the aligner (see FIG. 7a). Such a thermoformed bump 20 requires skillful manipulation of the pliers to form a bump 20 positioned in the wall of a tooth-receiving compartment of an aligner. When such a modified aligner is seated in position in the mouth, the location of the bump 20 is such that it produces a force vector to mechanically rotate the tooth.

To illustrate the use of such bumps in treatment, a disto-lingually rotated maxillary lateral left tooth may be rotated by placing a first bump 20 at the disto-incisal position to contact the tooth on its disto-lingual surface, and a second bump 20 formed at the mesio-labial, incisal location of the same compartment. During treatment, such a pair of co-working bumps cooperate to create a coupled rotational force in a mesial-lingual direction according to this example. The correction needed to fully correct a rotated tooth can be achieved by activating the aligner through using the appropriate Thermoplier as described. Progressive activation in this manner serves to counter force level reduction resulting from the dissipation of corrective forces as the teeth respond and move. Such revisions also serve to maintain more constant biological forces on the teeth being repositioned, which is generally thought to promote the most rapid tooth movement. A set of aligner trays 18 may be typically produced with programmed bumps in each aligner tray 18 for a course of treatment, as described above. However, in alternate embodiments a single aligner tray 18 may be modified, e.g., by adding features or enlarging existing features. One or more modifications will allow a single aligner tray 18 to serve for multiple progressive treatment phases before being spent and discarded.

Bumps as described serve to focus energy stored locally in the region of the aligner's structure adjacent to a bump 20. The inward-projecting bump 20 causes an outward flexing of the aligner material in a region away from the tooth surface. Configured in this way, bumps gather stored energy from a wider area and impinge that energy onto the tooth at the most mechanically advantageous point, thus focusing corrective forces most efficiently.

In another example, in which the tooth is essentially in its proper position and only requires torqueing to a desired orientation, a bump 20 may be installed near the incisal edge on the lingual side, the incisal edges of the crown will slowly respond by swinging into the relief of the window on the labial.

Commonly owned U.S. Pat. No. 6,702,575, entitled "Orthodontic Aligner Auxiliary System", teaches other techniques for extending the usefulness of aligners and is hereby incorporated by reference. The '575 patent involves the installation of separate auxiliary devices into the physical structure of conventional aligners and related methods for preparing aligners to accept and retain such devices. To follow is a description of how these devices may be incorporated into the overlay method and aligner trays 18 formed using the overlay method, along with descriptions of how they function and the preparatory steps that must first be taken so that such devices can be installed into an aligner's structure.

The '575 patent involves the introduction of a group of small devices that are intended to be strategically positioned and attached to an aligner's structure. Such devices are termed "aligner auxiliaries." Prior to installing such devices, a doctor may assess the progress of a case at mid-treatment, for example and in particular, make note of problem areas where the desired tooth response is lagging or instances where particular teeth are stubbornly not moving in response to treatment forces. Aligner auxiliaries are installed in those locations to amplify and focus corrective forces of the aligner to enhance correction. For example, an auxiliary known as a tack 30 (FIGS. 8*a*, 8*b*, and 8*c* ) can be installed after a hole of a predetermined diameter is pierced through a wall of a tooth-containing compartment of an aligner. The diameter of the hole is slightly less than the diameter of a shank portion of the tack. Next, a tack-installing plier is used to forcibly pop the retentive head of the tack 30 through the hole, resulting in the tight and secure retention of the tack within the aligner structure. The tack pops into position where it is tightly retained in the aligner within the punched hole. Such progressively-sized tacks and other auxiliary devices are commercially available to orthodontists who use them to augment and extend the tooth position correcting forces of aligners.

Figure 8A:
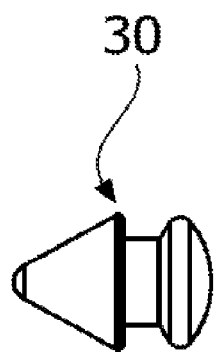
FIGS. 8a, 8b and 8c show an exemplary series of tacks.
Figure 8B:
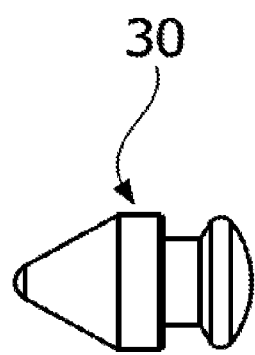
Figure 8C:
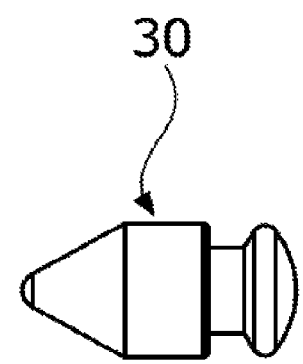

The installation of an auxiliary device such as a tack 30 to achieve the delivery of tooth-moving forces is similar to the effect achieved by installing the bump 20 described earlier. The use of a separate tack, however, permits the forces delivered to a tooth to be progressively regulated over time by using a sequential series of progressively longer tacks 30 as shown in FIGS. 8*a*, 8*b*, and 8*c* and described in the '575 patent. A series of aligner trays 18 may be generated, as is described above with respect to bumps. As the energy stored in the aligner's structure adjacent to the tack is spent through movement of the tooth, the aligner with the longest of three tacks can be installed after the medium tack is spent, removed and discarded.

Digital Overlay Method

Figure 9:
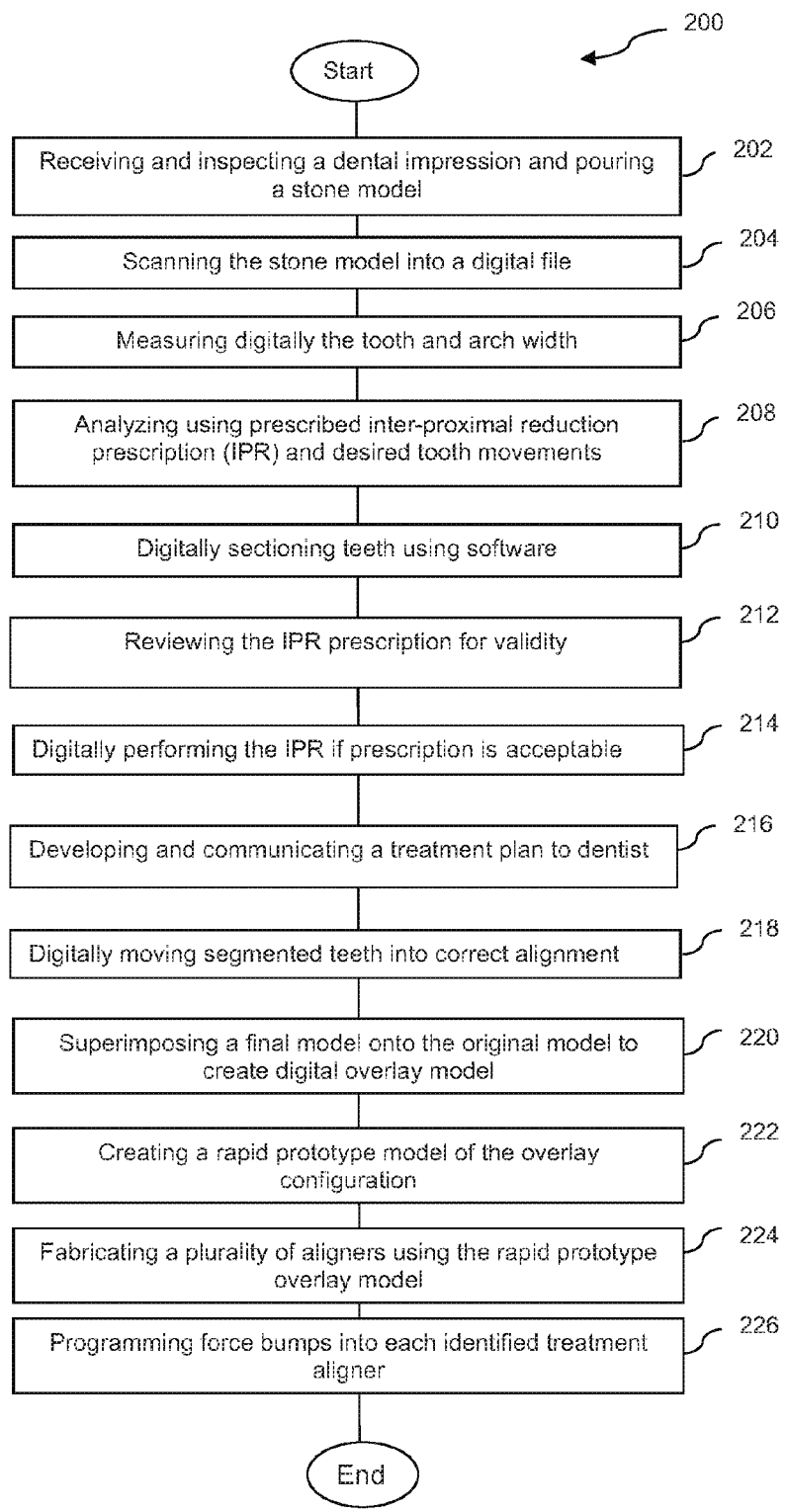
FIG. 9 is a flow chart of another embodiment of the overlay method of fabricating aligner trays using digital imaging.

Referring next to FIG. 9, in another aspect of the invention an overlay method of fabrication of aligners for orthodontic treatment may be implemented digitally, using the following method 200. Initially, a patient's dental impression is received and inspected. At step 202, a stone model 10 is poured from the impression. At step 204, the stone model is scanned into a digital format representing the original position of the teeth in the patient's maloccluded dentition, e.g., using a scanning software system such as 3Shape R700, by 3shape, a 3D scanner system developed to scan dental stone models. At step 206, the tooth and arch width are measured digitally, e.g., using Ortho Analyzer software. Next, at step 208, the patient's malocclusion is analyzed using prescribed inter-proximal reduction prescription (IPR) and desired tooth movements. At step 210, representations of the teeth are digitally sectioned using software, e.g., Ortho Analyzer Next Generation software from 3shape. In an alternate embodiment, the digital file may be created directly from an intra-oral scan of the patient's dentition, providing the original maloccluded dentition in a digital format without having to create and scan a stone model 10.

The method proceeds from step 210 to step 212, in which the IPR prescription is reviewed for validity. At step 214, IPR is done digitally if the prescription is acceptable, and necessary changes are approved by the dentist. At step 216, a treatment plan is developed and communicated to the dentist, using a set of clinical verification forms. At step 218, segmented representations of the teeth are digitally moved into correct alignment to create a final model 12. Final model 12 may then be scanned to create a final tooth position digital model. At step 220, the final tooth position digital model is superimposed with the original model to create a digital overlay model 14. The digital overlay model 14 may be suitable for rapid prototyping, e.g., using Materialise 3-matic. At step 222, a rapid prototype or physical overlay model 16 is created of the overlay configuration. The physical overlay model 16 is then created by a rapid prototyping method.

Next, at step 224, a plurality of identical aligner trays 18 are fabricated, e.g., using the physical overlay model 16. The physical overlay model 16 is used to create an aligner tray 18. The number of aligners varies from case to case. In one exemplary embodiment aligner tray 18 is preferably thermoformed over the physical model 16 using for example, using an Essix vacuum forming machine and Essix Ace plastic thermoforming sheets. As described above with respect to the manual overlay method, using the physical overlay model 16 to produce aligner tray 18, results in a clear pathway of space from the teeth positions before patient treatment to the teeth positions after treatment, created to allow for tooth movement, as was already discussed.

Figure 7B:
Figure 7C:
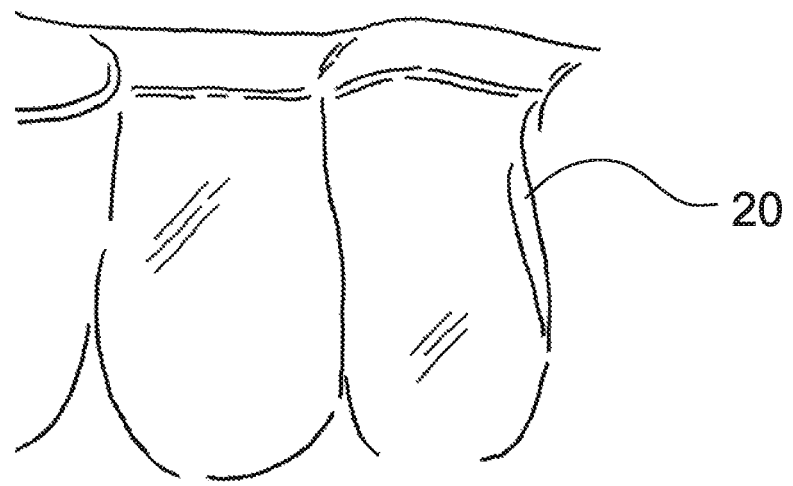

At this point in the fabrication process, aligner tray 18 is passive, i.e., aligner tray 18 will not exert forces on the teeth when inserted into the patient's mouth. The original and the final tooth positions as well as the pathways for each tooth fall within the boundaries of the aligner. The aligner trays 18 are then thermoformed using the overlay model 16. Each aligner tray 18 is identified as step 1, 2, 3, etc. The resulting aligner tray 18 does not actively engage any single tooth for inducing tooth movement, but generates a passive aligner tray 18 with which preselected individual teeth can be moved. Movement of the preselected individual teeth is induced by programming or forming features in the passive aligner, such as bumps 20, to apply pressure to teeth (see FIGS. 7*a*-7*c*). Features may be formed using the patented Hilliard thermoforming pliers system.

After thermoforming aligner trays 18, at step 226, force bumps 20 are programmed into each identified treatment aligner tray 18, as described above with respect to the manual overlay method.

Programming force bumps 20 into aligner trays 18 may be done by manually thermoforming each bump 20 in the lab using a thermoforming tool, for example, a Hilliard Thermopliers®, by DENTSPLY Raintree-Essix, of Sarasota, Fla. Aligner trays 18 that are thermoformed from overlay models 16 may be manually adjusted with the force bumps 20 using the Thermopliers®. Aligner trays 18, inclusive of the manual force bumps 20 are then sent to the dental professional. After the final aligner configuration is inspected, a final retainer is thermoformed using final model 12, and then aligner trays 18 and final retainer are shipped to the dentist.

In one embodiment the stone models of the patient's dentitions may be scanned and stored in a digital computer-aided-design (CAD) file format. The patient's models are then subjected to a scanning process and the resulting data for the upper and lower arches is stored in digital format to create a CAD model of at least a portion of the patient's dental anatomy. The most frequently used means of converting an actual physical object into digital code for three-dimensional imaging, namely laser scanning, as well as other methods, first produce what is known as a "point cloud". The software will strive to rationalize the location of points known to be associated with features of the actual object with that same point located in other scans obtained while scanning the object from multiple angles. All of the points taken from multiple scans from different vantage angles will be overlapped and interpreted, allowing the software to create a complex surface represented by a cloud of perhaps a half-million individual points. Each of the points is assigned specific coordinates in three-dimensional space relative to a predetermined point of origin on the physical stone model of the patient's teeth. It should be understood that all of the points theoretically fall on the surface of the part being imaged and by viewing all of the points, a rough sort of visual image of the original part can be seen visually on a computer monitor.

Figure 10:
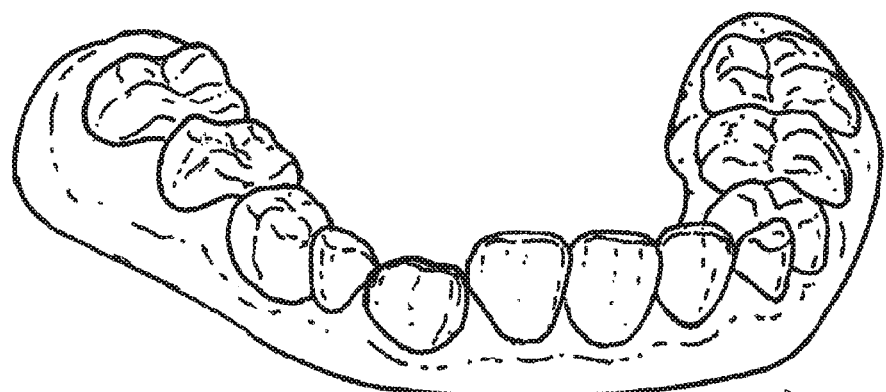
FIG. 10 shows a CAD image of the patient's teeth.

Other software available to a CAD technician can be used to further process the point cloud into what is known as a true solid model that can be later manipulated and modified using solid-modeling CAD software. FIG. 10 is an example of the resulting CAD image 15 of the patient's teeth. However, some of the operations that a CAD technician needs to accomplish in processing an orthodontic patient's case can be performed at the initial point cloud phase.

Figure 11:
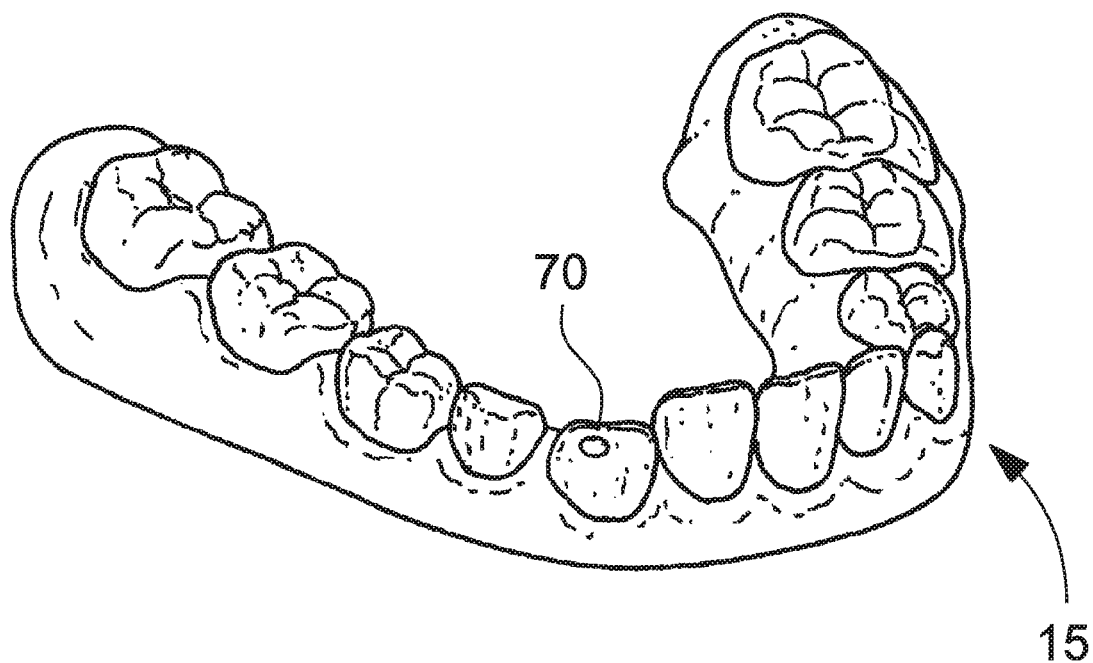
FIG. 11 shows the CAD image of the patient's teeth from FIG. 10 including a force bump.

As an example of how a point cloud can be manipulated according to the present invention, commercially-available software permits a CAD technician to identify a region of points. The points inside such a region are assigned different properties than unaffected points outside the region. For example, a CAD technician may identify a region of points representing the occlusal region of a particular tooth from a scanned-in set of models. That region of points may be approximately the same size as an inwardly extending bump 20 or outwardly extending bubble, for example. Conventional algorithms affecting how points within the identified region are dynamically linked allow the technician to grab any one point located near the center of the region and that point is then considered a master point. For example, the technician would accomplish this through manipulation of a digitizing puck on a digitizing tablet or with a mouse. The technician would tug on that master point. When tugged, all of the surrounding linked points within the identified region will to one degree or another move along with the master point being tugged in proportion to their relative distance from the master point. For example, points relatively near the master point will move the most whereas points more remote from the master point will move only a little. From this action, all of the points within the identified region will move to one degree or another and thereafter, the points inside the region will have moved inward into the general shape and appearance of a force bump 20 as shown in FIG. 11.

Similarly, an outward-extending bubble can be formed by the technician by pulling a master point rather than pushing. Again, all of the points in a region will tag along to one degree or another as determined by the logic of how the points within the region are dynamically linked.

As an alternative a hand-held scanning wand (e.g., the Orometrix®system) can be used in the orthodontist's office to directly scan the patient's oral anatomy. The resulting digital data is then electronically transmitted to the orthodontic service center. Similarly, it is possible for the scanning methods described above to be directed to scanning the concave negative troughs directly from a set of dental impressions.

Figure 16C:
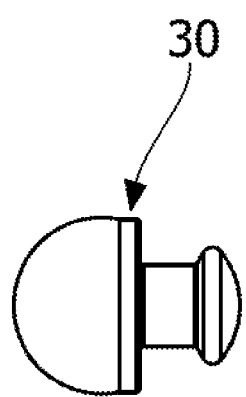
FIGS. 16a, 16b and 16c show an exemplary series of an alternate form of tacks.
Figure 16B:
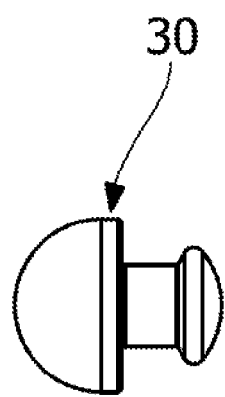
Figure 16A:
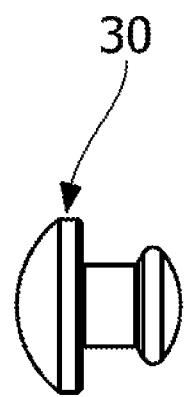

Due to the many degrees of activation afforded by the array of various types of direct aligner alterations that can be made, such as with Thermopliers®, and the array of separate auxiliary devices, progressive tooth movement may be achieved through the use of an overlay aligner tray 18 having the hybrid original and final geometries combined. Multiple aligner trays 18 of the singular overlay aligner tray 18 can then be sequentially programmed to include bumps, or tacks, inserts and the like, as described above. For example, direct tooth contacting short, medium and long tacks 30 (FIGS. 8a, 8b and 8c ) may be used, or other devices with sequential elasticity (FIGS. 16a, 16b, and 16c ) may be used. Various threaded devices may be progressively activated, as can a jackscrew. Stainless steel or metallic auxiliaries such as a cantilever arm can be progressively activated over time as is typical of orthodontic hardware. In this manner, aligner trays 18 produced according to the present inventive methods can be considered as "progressive" in orthodontic treatment.

As a technician analyzes a patient's models visible on the computer monitor, the technician would see images representing a malocclusion at the beginning of treatment or partially-treated occlusion. Since the models can be used to generate a true three-dimensional image of the patient's oral anatomy, as shown in FIG. 10, the technician can dynamically rotate the dental topology for close scrutiny. The technician can sight across the virtual teeth from literally any angle or vantage point, including vantage points that would be anatomically impossible with a living patient, such as viewing from the rear of the mouth or vantage points occluded by bone and tissue.

Figure 12:
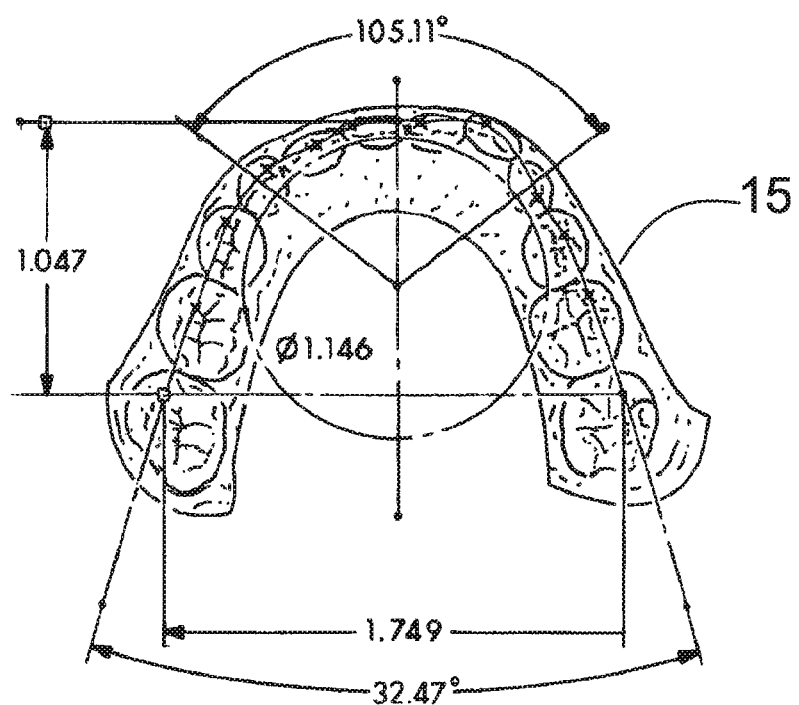
FIG. 12 shows the CAD image of the patient's teeth from FIG. 10 including reference lines, centerlines, and two-dimensional and three-dimensional splines.

Since the model exists in a virtual three-dimensional CAD space, the technician can assess the case and take measurements to quantify various criteria for treatment, such as upper versus lower arch length, arch width, inter-canine width, arch morphology as well as degree of open/deep bight, molar relationship, over jet, curve of Spee, and symmetry. The technician can also note primary, deciduous, missing and impacted teeth, and consult statistical anatomical values, all in light of the attending doctor's instructions/prescription. For example, the CAD software can be used by the technician to sketch any number of reference lines, centerlines, and such, as shown in FIG. 12. The dentition can be interrogated just like any solid model can be dimensioned with CAD software. As depicted in FIG. 12, two-dimensional and three-dimensional splines may be strung between features of the scanned-in surfaces. The technician may zoom in and magnify particular features for examination and decision making. Any number of features may be dimensioned from technician-specified reference lines or relative to other features of the anatomy. Generally, based on this process of measuring and examination, a technician may thereafter refer to and use known statistical data of established anatomical dental norms or other norms such as typical torque, tip prominence and arch form values found in patients of the same age, sex and ethnic characteristics. All of these activities are undertaken to arrive at optimal decision-making in preparation to designing a number of aligners and aligner auxiliaries to achieve treatment objectives.

A CAD technician can make decisions such as where best to form various bumps, bubbles, windows, various holes for activation devices, standoffs and outset lands and so on, that together will serve to activate tooth movement, as well as locate the myriad of aligner auxiliaries 30 described above, with the aid of all of the technology and digital tools available at his or her disposal. The technician has analytical, measurement, and investigative tools at hand. Thus the technician can determine where to locate aligner features such as inwardly extending bumps. Various types of aligner auxiliaries 30 can also be optimally located by the CAD technician.

For example, the technician may identify a labially-flaired anterior tooth that requires uprighting. To accomplish such a correction with a suck-down aligner, the technician may opt to have a tack located at an exact position relative to that tooth. The technician will determine the ideal location that will maximize the tack's mechanical advantage for uprighting, and a location indicator (e.g., a divot marker 32) will be created exactly at that point. For that matter, the optimal location for piercing the aligner for the full array of aligner auxiliaries can best be determined by the CAD technician rather than the doctor attempting such an analysis manually while simultaneously addressing all of the other concerns and distractions involved when working with a real patient.

In general, the technician manipulates the CAD model to create a progressive series of aligners with features for accommodating aligner auxiliaries for sequential use during the patient's orthodontic treatment. The technician working with the CAD system can create multiple virtual models representing the incremental, but progressive movement of teeth between the "as scanned" occlusion and the desired final occlusion. In addition, the technician can use the CAD system to move specific teeth according to treatment objectives to desired positions as would be considered ideal at the end of a specific phase of treatment for which aligner auxiliaries are to be employed. Movements accomplished by the CAD technician can include correction of individual teeth in terms of torque, tip, prominence, rotation, bodily movement, and to a degree, intrusion and extrusion.

Figure 13:
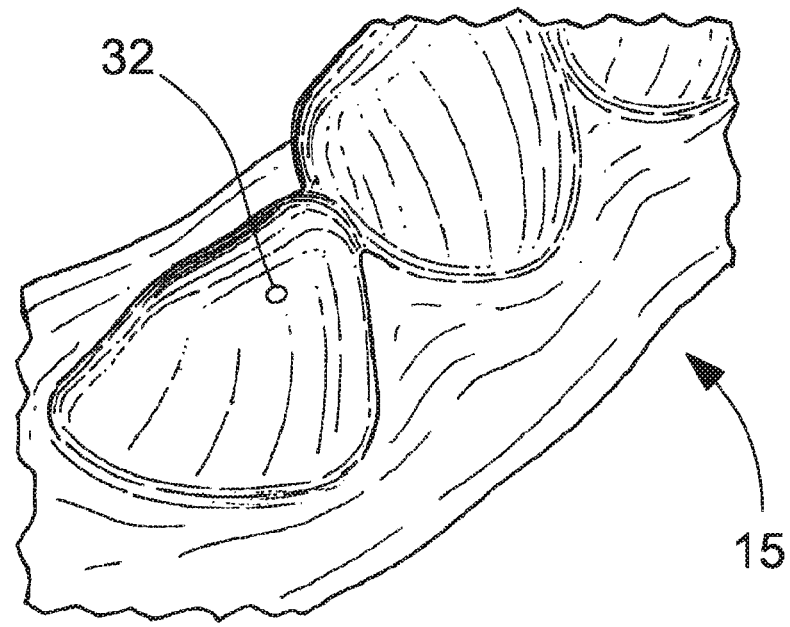
FIG. 13 shows a section of the CAD image of the patient's teeth from FIG. 10 including a divot marker.

For example, the technician has the capability of zooming in on fine detail so that the computer monitor and the technician's field of vision accommodate only a single tooth being analyzed. In order to establish the optimal location for aligner auxiliaries, such as the pop-in tacks, a divot marker 32 can be installed on the model by the technician, as depicted in FIG. 13. A divot marker 32 is very similar to an inwardly extending force bump 20 in FIG. 11, but it is spherical rather than elliptical and much smaller in diameter. To form a divot marker 32, the technician will identify a small round region of the point cloud at exactly the right position relative to the tooth under scrutiny. The technician will select and push a master point near the center of the region and all linked points will follow to a degree. The result is a series of discrete, sharply formed concavities located here and there as required around the arch to serve as visual markers indicating the position where holes will be installed relative to mal-positioned teeth.

Figure 15:
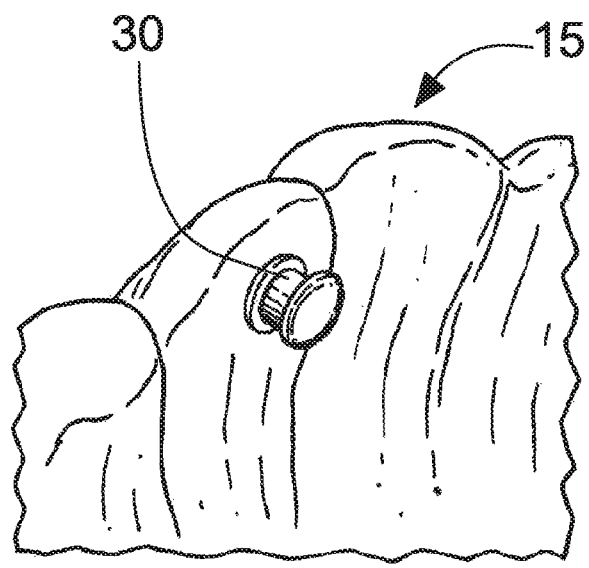
FIG. 15 shows a tack and the virtual model as one solid structure.

Another point cloud-based operation is that of locating retaining tacks 30, as described in FIG. 15, that serve to hold the entire aligner tray 18 in place in the mouth. In summary, technician-located marker divots would serve to mark locations for later installing pliers-formed holes for the installation of the various types of aligner auxiliaries described above. If the technician decides that an aligner tray 18 will be cut into multiple sections, a series of divots can be used to mark the location of the cuts or sinuses.

Preparing the model to form aligners with windows or outset lands requires methods that are different than those used to form bumps, bubbles and marker divots. Windows usually will have a plan-form or outline following the edges of a portion of the crown of a tooth or the entire crown of a tooth. Such shapes are more Cartesian than football-shaped bumps, bubbles and the round divot markers, and generally larger. Nonetheless, the CAD technician employing the methods of the present invention can form a polygonal boundary around the region of involved points of the point cloud, again creating a region that includes the linking of all of the points inside that boundary. Using a different point-linking algorithm however, the CAD technician can tug on a master point and all of the linked points of the point cloud within the designated region will follow equally. The point-linking logic will result in the entire region standing outward from the tooth surface. Such a feature will later be present in the actual formed aligner and will serve as a physical template or aid to the doctor or lab technician in cutting away aligner material to form a window. Since it is a raised plateau formed directly in the aligner, the doctor can easily see what material the technician had decided was necessary to remove.

As described above, elastic hooks and other aligner auxiliaries that pop-in can be installed in an outset land in order to ensure that their inwardly extending features do not contact teeth. In establishing outset lands on the virtual model, the technician will use the same point-linking algorithms as used for establishing the shape and location for a window where all of the points come along with a tugged master point equally.

Figure 14:
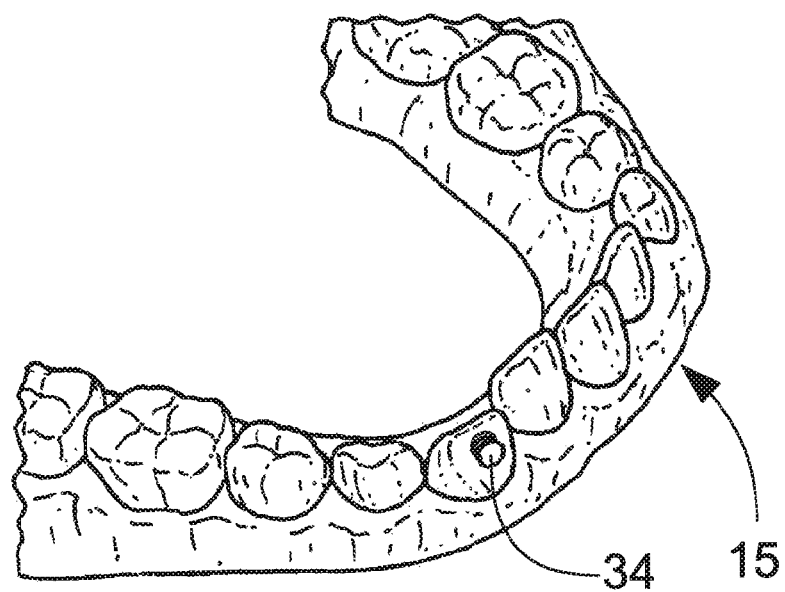
FIG. 14 shows an exemplary retaining tack, also referred to as aligner auxiliary.

As shown in FIG. 14, a round outset 34 has been formed by identifying a circular region of points and tugging all of those points outward perpendicularly away from the tooth surface. As can be appreciated, when an aligner is sucked down over such a pattern, a corresponding outset land will be formed in the aligner. Once formed in the aligner, a hole can then be pierced at the center of the flat top of the outset using a special pliers, such as catalog item 82730, available from Raintree-Essix, Metairie, La. Once a hole is pierced, any one of a group of pop-in aligner auxiliaries can be installed as needed.

As previously described, tacks may be offered in a progression of lengths characterized as short, medium and long. In such a series, the increase in length between a short tack and a medium tack and then to a long tack may be about 0.75 mm. In a case where, for example, a tooth needs only a slight correction, or the exact amount of correction needed falls in between the 0.75 mm increments between short, medium and long, a CAD technician may construct a discreet outset land of a precisely controlled height. For example, if a very short outset land were to be formed with a height of 0.37 mm, and a medium tack was installed in the outset land, the forces applied to the underlying tooth would be equal to a tack falling approximately half way between a short and medium tack. In this manner, devices of predetermined force-generating dimensions may be further calibrated as needed by mounting them in outset lands of selected heights.

Continuing with aspects of the present invention that lend themselves to very precisely controlled corrective movements of teeth such as those finishing corrections needed to attain final aesthetic positioning at the end of treatment, the following method is described through the example of a lower incisor that is undesirably inclined lingually by 1 mm. A CAD technician can form a virtual depression, similar to a divot or the depression associated with a bump 20, but sized and shaped to accommodate the nose of a tack. Such a geometrically discrete depression will be formed on the lingual side of the virtual tooth near its incisal edge. The CAD technician will form the depression in the lingually inclined lower incisor with a depth corresponding exactly to the amount of correction needed, in this case 1 mm deep. After the depression has been formed, the CAD technician will bring a virtual model of a medium tack into the virtual space and move it into close proximity with the depression. Using a CAD step known as "mating", the CAD technician will cause the nose of the tack to come into intimate contact with the depression so that the tack 30 and the virtual model become one solid structure, as shown in FIG. 15.

When a suck-down pattern is produced from this virtual model and an aligner is then sucked down over it, the resulting aligner will exhibit an outset feature adjacent to the undesirably lingually-oriented tooth coinciding with the exposed portions of a tack projecting lingually out of the referenced mandibular incisor. When viewing the aligner (particularly that cavity from the inside), it will be seen that the lingual-outset feature extending lingually from the subject lower incisor will have internal dimensions exactly corresponding to the exposed portions of the tack 30. The resilient nature of the aligner material permits the forcible placement of a tack into this outset feature. The tack will then be held and retained within the recess.

Most of the foregoing descriptions of various actions and operations that can be executed by a CAD technician in preparing aligners have involved manipulations of the initial digital point cloud. Other types of operations that a CAD technician may need to undertake can best be accomplished after the point cloud has been further processed. Since such operations involve the use of CAD software to construct precise features on the virtual model, the first step in such a process is to convert the point cloud data into a surface, and then into what is known as a solid model. Software suitable for converting raw point cloud data into complex biological surfaces are available for this purpose from the sources listed below: Raindrop Geomagic, Inc. P.O. Box 12219 Research Triangle Park, N.C. 27709 Lightwave Enterprises, Inc. 2396 Innovation Way Rochester, N.Y. 14624 Paraform, Inc. 3052 Bunker Hill Santa Clara, Calif. 95054. Once the point cloud has been converted to a surface, the software is further used to close the surface. "Closing" here indicates it should be understood that the teeth and a small portion of the gums form a generally horseshoe shape. The surface defining the gums and teeth is in a mathematical sense infinitely thin. In CAD terminology, it is referred to as "lightweight". If the lightweight horseshoe-shaped dental model is viewed from its rear surface, for example, it is seen as merely a hollow shell. The software, in closing the surface, in effect puts a bottom on it. At this stage it may still be considered an infinitely thin surface (i.e., lightweight), but with a bottom on it, it takes on a quality known as "watertight".

CAD software of the solid-modeling type such as is available from SolidWorks Corporation, 300 Baker Avenue, Concord, Mass. 01742 and PTC (Pro-Engineer), 140 Kendrick Street, Needham, Mass. 02494, has the capability of taking lightweight but watertight surfaces and converting them into standard, fully dense or fully solid models of the type normally handled by solid modeling CAD software. Once converted to such a solid, the resulting dental model can be manipulated in a CAD environment in a conventional manner.

One of the operations that a CAD technician would then undertake according to the methods of the current invention is the installation of structures emerging directly out of the virtual solid CAD model. For example, a structure may be constructed that is needed for draft-retained inclusion devices. Two basic types of aligner auxiliaries were described above. One group of aligner auxiliaries were described as pop-in and a second group was described as devices that must be installed in outset lands to prevent them from undesirably contacting teeth. A third group of aligner auxiliaries referred to as "draft-retained devices" can also be accommodated with the present invention. Modification of the CAD model for attachment of draft-retained devices is preferably done after the point cloud has been converted to a solid CAD-manipulatable model. CAD manipulations of a solid model are precise and generally more sophisticated than operations involving the tugging or pushing on a point cloud.

As noted above, embodiments within the scope of the present application include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

It should be noted that although the figures herein may show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the application. Likewise, software implementations could be accomplished with standard programming techniques with rule based logic and other logic to accomplish the various connection steps, processing steps, comparison steps and decision steps.

It will be appreciated therefore, that the present invention provides a new and useful method and apparatus for orthodontically aligning teeth. The method steps and the equipment, components, software and the like can, of course, be changed or varied and still fall within the scope of the invention. The invention has been exemplified as described herein and as shown on the drawings, and the actual scope of the invention shall only be limited by the attached claims.

The invention claimed is:

1. A method of fabricating an orthodontic aligner tray comprising:
   segmenting teeth represented by an original digital model of a patient's teeth;
   repositioning at least one of the teeth represented by the original digital model from an original position to a final position to create a final digital model of the patient's teeth, the final digital model representing a final teeth position to be achieved by an orthodontic treatment plan;
   superimposing the final digital model onto the original digital model to create an overlay model;
   fabricating a plurality of identical aligner trays based on the overlay model, each tray having a tooth-receiving compartment such that the original position, final position, and a movement pathway from the original position to the final position are within the tooth-receiving compartment of the aligner and forming the plurality of identical aligner trays as passive aligner trays;
   identifying a position for a first force appliance in a first aligner tray; identifying a position for a second force appliance in a second aligner tray; and
   inserting the first and second force appliances into their corresponding aligner trays, the first and second force appliances positioned within the tooth-receiving compartment of its corresponding aligner tray to exert a selected force upon a tooth to be repositioned.

2. The method of claim 1, wherein the step of fabricating comprises creating a rapid prototype model of the overlay model.

3. The method of claim 2, wherein creating the rapid prototype model is performed by one of stereolithography, laser sintering or fused deposition.

4. The method of claim 1, wherein the original digital model of a patient's teeth is obtained by pouring a stone model from a patient's dental impression and scanning the stone model into a digital file.

5. The method of claim 1, wherein the original digital model of a patient's teeth is obtained by performing an intraoral scan of the patient's dentition.

6. The method of claim 1, further comprising analyzing a case using an inter-proximal reduction (IPR) prescription and desired tooth movements.

7. The method of claim 6, wherein the step of analyzing comprises reviewing the IPR prescription for validity; performing IPR if the IPR prescription is acceptable; and developing the orthodontic treatment plan.

8. The method of claim 1, wherein the step of fabricating the aligner trays further comprises vacuum thermoforming the aligner trays over a physical representation of the overlay model using a vacuum forming machine and a plastic thermoforming sheet.

9. The method of claim 1, wherein the step of identifying a position for the first force appliance in the first aligner tray comprises digitally establishing a divot marker on a digital model of the patient's teeth intermediate the original digital model and the final digital model.

10. The method of claim 9, wherein the step of digitally establishing the divot marker comprises identifying and selecting a master point near a center of a desired region on the digital model of the patient's teeth at a point intermediate the original position and the final position within the overlay model.

* * * * *